US007805180B2

(12) United States Patent
Steckner

(10) Patent No.: US 7,805,180 B2
(45) Date of Patent: Sep. 28, 2010

(54) METHOD OF MODIFYING MR SIGNALS USING ULTRASOUND WAVES

(75) Inventor: Michael Steckner, Richmond Heights, OH (US)

(73) Assignee: Hitachi Medical Systems America, Inc., Twinsburg, OH (US)

( * ) Notice: Subject to any disclaimer, the term of this patent is extended or adjusted under 35 U.S.C. 154(b) by 630 days.

(21) Appl. No.: 11/675,859

(22) Filed: Feb. 16, 2007

(65) Prior Publication Data

US 2008/0200795 A1 Aug. 21, 2008

(51) Int. Cl.
*A61B 5/05* (2006.01)
*G01V 3/00* (2006.01)
(52) U.S. Cl. ...................... 600/411; 324/309
(58) Field of Classification Search ........................ None
See application file for complete search history.

(56) References Cited

U.S. PATENT DOCUMENTS

| 5,247,935 | A |   | 9/1993  | Cline et al.   |         |
|-----------|---|---|---------|----------------|---------|
| 5,291,890 | A |   | 3/1994  | Cline et al.   |         |
| 5,402,786 | A | * | 4/1995  | Drummond       | 600/410 |
| 5,553,618 | A | * | 9/1996  | Suzuki et al.  | 600/411 |
| 6,148,225 | A | * | 11/2000 | Kestler et al. | 600/411 |
| 6,246,895 | B1 | * | 6/2001  | Plewes         | 600/410 |
| 6,735,461 | B2 |   | 5/2004  | Vitek et al.   |         |
| 2002/0188193 | A1 | * | 12/2002 | Biglieri et al. | 600/411 |
| 2002/0193681 | A1 |   | 12/2002 | Vitek et al.   |         |
| 2003/0083573 | A1 | * | 5/2003  | Azuma et al.   | 600/411 |
| 2003/0088176 | A1 | * | 5/2003  | Unger          | 600/411 |
| 2004/0267111 | A1 |   | 12/2004 | Feinberg       |         |
| 2007/0167705 | A1 | * | 7/2007  | Chiang et al.  | 600/407 |

OTHER PUBLICATIONS

Rousseau, J., et al., Acoustic NMR in Liquids, Paper presented at the Society of Magnetic Resonance in Medicine, 1986.

* cited by examiner

*Primary Examiner*—Long V Le
*Assistant Examiner*—Angela M Hoffa
(74) *Attorney, Agent, or Firm*—Ulmer & Berne LLP

(57) ABSTRACT

Described herein is a medical imaging technique that includes directing ultrasound waves into a portion of a body of interest during at least a portion of a time period during which an MR imaging process is simultaneously performed on the portion of the body of interest such that the MR signal is altered by the application of the ultrasound waves. The ultrasound waves may be applied continually during the MR imaging process, or only during a portion thereof. The frequency of the ultrasound waves may be substantially the same as, or different than that of the MR signals. Images may be produced from only the MR imaging process or both the MR imaging process and the application of ultrasound waves prior to the imaging sessions.

8 Claims, 5 Drawing Sheets

METHOD OF MODIFYING MR SIGNALS USING ULTRASOUND WAVES

TECHNICAL FIELD

The invention relates generally to magnetic resonance signals, and more specifically to the modification of such signals by ultrasound energy.

BACKGROUND OF THE INVENTION

Magnetic resonance imaging (MRI) is a medical diagnostic imaging technique that is used to diagnose many types of injuries and medical conditions. An MRI system includes a main magnet for generating a main magnetic field through an examination region. The main magnet is arranged such that its geometry defines the examination region. The main magnetic field causes an alignment of the magnetic moments of the nuclei within the body to be aligned with a net result in a parallel orientation. The main magnetic field causes the protons to rotate around the equilibrium axis with a frequency, known as the Larmor frequency, that is characteristic for the nuclei to be imaged. An external radiofrequency (RF) field applied by other hardware within the MRI system perturbs the magnetization from its equilibrium state.

Upon termination of the application of the RF pulse, the magnetization is relaxed to its original position. The exponential time rate at which the nuclei to relax to its original position is often referred to as the spin-lattice relaxation time, or T1; the exponential rate at which the nuclei mutually diphase is often referred to as the spin-spin relaxation time, or T2. During relaxation the rotating magnetic moment induces a time varying voltage in the receive coil that can be detected. An image processor then reconstructs an image representation from the received magnetic resonance signals for display on a human readable display.

Magnetic resonance elastography (MRE) is a technique that combines the use of a mechanical actuator agitating the tissue of the body with MR imaging. A mechanical actuator creates waves between 100 to 1000 Hz within the tissue of interest, and imaging by the MR imager is gated or otherwise synchronized to that frequency, as MR images are motion-sensitive. The differing shear modulus, or softness, of each type of tissue promotes a different wave pattern within the tissue caused by the agitation of the mechanical waves. The technique promotes detection of subtle changes in tissue displacement and determines the mechanical tissue properties quantitatively. This is especially beneficial in the diagnosis of disorders that have a characteristic stiffness of a region of tissue with respect to the surrounding tissue, and is important in the diagnosis of many thyroid, prostate, breast and abdominal pathologies.

Ultrasound energy is commonly used in ultrasound imaging, which is alternatively known as ultrasound scanning or sonography. Ultrasound imaging is another type of medical imaging, and uses high-frequency sound waves to obtain images of the human body. The high-frequency sound waves are directed into the human body using an ultrasound transducer. The injected sound waves echo from the body's tissues and fluids, reflecting back into the probe, which is commonly a crystal attached to electrodes. The strength and characteristics of the reflected waves are recorded and the ultrasound system calculates the distance of the tissue from the probe and displays a real-time image of the tissues and fluids.

Ultrasound has many limitations, including difficulty of the ultrasound waves penetrating bone and gassy areas of the body containing air. Thus, internal characteristics of bone, the stomach and the intestines may not be properly imaged. Ultrasound waves rapidly loose strength as the distance of penetration increases. This may cause difficulties when imaging the deeper structures of the heart and abdomen areas, as well as difficulties in imaging obese patients. Also, the depth of ultrasound penetration rapidly decreases as the frequency of the waves is increased. However, ultrasound imaging can be quantitative, so as the small differences between two images taken at different depths of the tissue, wherein the second image is taken with the transducer applying more pressure to the tissue, can be used to establish the mechanical characteristics of the tissue.

Prior Art has combined the use of ultrasound with the use of MR. Examples can be seen in U.S. Pat. No. 5,247,935, U.S. Pat. No. 5,291,890, U.S. Pat. No. 6,735,461, and US Application Publication 2004/0267111. The past combination of ultrasound and MR has focused primarily on using the heat characteristics of the combined waves to destroy certain tissues within a patient's body, and using the combined methods for MR scan navigation. To date, no Prior Art has provided an effective method of using ultrasound waves to modify the MR signal characteristic primarily through altering the contrast of the MR images.

SUMMARY OF THE INVENTION

The invention of this application provides a process whereby ultrasound waves are utilized to direct acoustic energy at or near the resonant frequency into a body during a low-field or mid-field MR imaging process. The application of the ultrasound waves throughout the MR imaging process alters the contrast of the ensuing clinical images.

It is an object of this invention to describe a process of modifying MR signals with ultrasound waves to promote the detection of the mechanical characteristics of tissues within the body.

It is yet another object of this invention to describe a process of modifying the contrast of clinical images produced using MR Imaging techniques by the additional application of ultrasound waves.

It is a further object of this invention to describe a process of modifying MR signals with ultrasound waves to increase the detection of tumors and other tissue disorders by use of a single medical imaging process.

It is yet another object of this invention to describe a process of modifying MR signals with ultrasound waves to provide a dual modality imaging process for efficiency in clinical diagnosis.

It is a further object of this invention to describe a process of modifying MR signals with ultrasound waves to accelerate the image rate.

It is another object of this invention to describe a process of modifying MR signals with ultrasound waves to modify image contrast characteristics and introduce new types of contrast based upon tissue properties and sound couplings.

These and other objects of the present invention will become more readily apparent from a reading of the following detailed description taken in conjunction with the accompanying drawings wherein like reference numerals indicate similar parts, and with further reference to the appended claims.

BRIEF DESCRIPTION OF THE DRAWINGS

The invention may take physical form in certain parts and arrangements of parts, numerous embodiments of which will be described in detail in the specification and illustrated in the accompanying drawings which form a part hereof, and wherein.

DETAILED DESCRIPTION OF THE INVENTION

Figure 1:
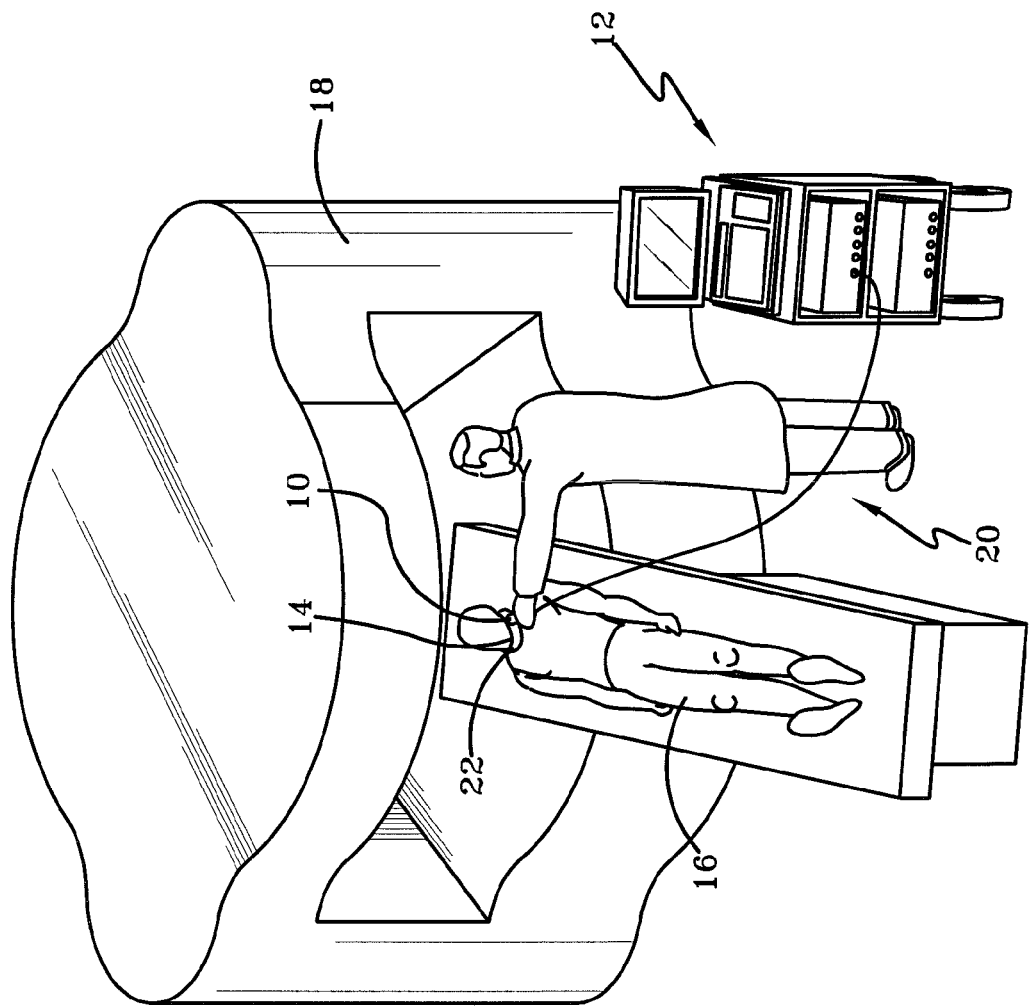
FIG. 1 is a perspective view of an embodiment of this invention wherein an ultrasound system is utilized to apply ultrasound waves to a portion of the body of the patient within the MRI system during the MR Imaging process.

Referring now to the drawings wherein the showings are for purposes of illustrating numerous embodiments of the invention only and not for purposes of limiting the same, the figures illustrate the novel idea of modifying MR signal with the use of ultrasound waves.

The process of an embodiment of this invention includes using ultrasound waves to direct acoustic energy at or near the resonant frequency into a body of interest, such as a patient, during a low-field or mid-field MR imaging process. The addition of ultrasound energy to differing tissue types having the same relaxation properties would cause an added MR image contrast discrimination based on tissue ultrasound and mechanical related properties increasing the quality level of the clinical images being generated from the MR scan. By applying acoustic energy at the Larmor frequency, the spin-lattice relaxation mechanism would be altered, changing T1 relaxation rates. The effect of this contrast discrimination would be useful in the detection of certain types of tumors, namely breast tumors, as a wider variety of tumors would be detected, including the tumors previously detectable only using MR imaging, along with the tumors previously detectable only using ultrasound imaging. The effects of this process would be similar to the effects of MRE imaging, however the frequencies and mechanisms of implementation vastly differ between the methods.

It is foreseen within this invention, as shown in FIG. 1, that ultrasound probe 10 is used to apply acoustic ultrasound waves generated by ultrasound system 12 to portion 14 of body 16 being imaged during the whole MR imaging process. It is also foreseen that application of the ultrasound waves may occur during just a portion of the imaging process. The MR imaging process uses magnetic resonance imaging (MRI) scanner 18, and a combination of other hardware and software (not shown) to produce clinical images of body 16. A commercially available ultrasound system capable of meeting the specifications of this invention can be used in combination with a commercially available MRI system capable of meeting the specifications of this invention. Specially designed ultrasound and MRI systems may also be used to implement the medical imaging technique of this invention. The process of this invention may also be implemented with the use of a specially designed combination system, with the single system having the hardware and software necessary for both MR imaging and ultrasound imaging combined in the same system.

One embodiment of the invention of this application involves using ultrasound probe 10 to apply ultrasound waves to portion 14 of body 16 throughout the entirety of the MR imaging process. The ultrasound waves may be applied by technologist 20, through the manual positioning of ultrasound probe 10, as shown in FIG. 1. The application of the ultrasound waves is not limited, however, to manual positioning of the ultrasound probe by the technologist. Further examples of the method of applying the ultrasound waves include, but are not limited to utilizing an ultrasound probe positioned within a gel bag that is positioned on a portion of the body before or during the MR imaging process. The ultrasound probe may also be manually positioned on or near a portion of the body being imaged, and temporarily secured to or near the portion of the body being imaged using methods such as adhesive, mechanical securing bounds, or any other securing means. The ultrasound probe may also be automatically positioned using any standard or custom ultrasound probe positioning system.

In one embodiment of the invention, portion 14 of body 16 will be surrounded by RF coil 22 during the scanning procedure. The constant application of ultrasound waves using ultrasound system 12 would lower the T1 of the MR imaging process, as well as alter the image contrast of the clinical MR images compared to the same clinical images taken without any ultrasound waves applied. However, limitations exist when ultrasound waves are applied throughout the whole MR Imaging procedure, as the efficiency of the RF pulse during MR imaging would be decreased, and it would become necessary to alter the MR sequence parameters to compensate for the altered T1.

In further embodiments of the invention, it may be preferable to alter the application of the ultrasound waves during the MR imaging sequence to some extent. The alteration of the ultrasound waves during the MR sequence could include gating, turning off, partially reducing the power, or substantially reducing the power of the ultrasound waves during the various phases of the MR sequence. For example, the ultrasound waves may be applied at a first power level during at least one period of time during which no RF pulse is being applied during the MR imaging process and may be applied at a second power level during at least one period of time during which at least one RF pulse is applied during the MR imaging process In a further embodiment, it may also be beneficial to reduce or remove the application of the ultrasound waves during data sampling as the waves would increase signal decay and increase noise into the receiver during sampling. The ultrasound waves may be applied at a first power level during at least one period of time during which no data sampling occurs during the MR imaging process and may be applied at a second power level during at least one period of time during which data sampling occurs during the MR imaging process.

Alternatively, sequences with a very long T1, such as Inversion Recovery (IR) sequences, may benefit from the decrease in T1. Similarly, the application of the ultrasound waves during the period after the data sampling may also depend on the sequence being used for imaging. For T2 or proton-density weighted sequences, the ultrasound may be appropriate to shorten the relaxation time requirements and decrease the imaging time after data acquisition.

Though ultrasound is commonly referred to as using high-frequency waves, the highest frequency range typically used for ultrasound applications is equivalent to the lower ranges of frequency typically used for MR applications, as ultrasound penetration rapidly decreases as the frequency is increased. The process of using ultrasound waves to modify MR signals would be most clinically useful when using the higher ranges of high-frequency ultrasound waves to modify low and mid-range MR frequencies, from the lowest of frequencies up to the frequencies utilized by a 0.3 T system. It is foreseen that the teachings of this invention may be used on higher-field applications should technology advance such that ultrasound systems become capable of producing higher frequency ultrasound waves with effective penetration. This depth limitation with MR frequency may not greatly affect the imaging of certain tumors close to the skin surface, such as breast tumors.

Figure 2:
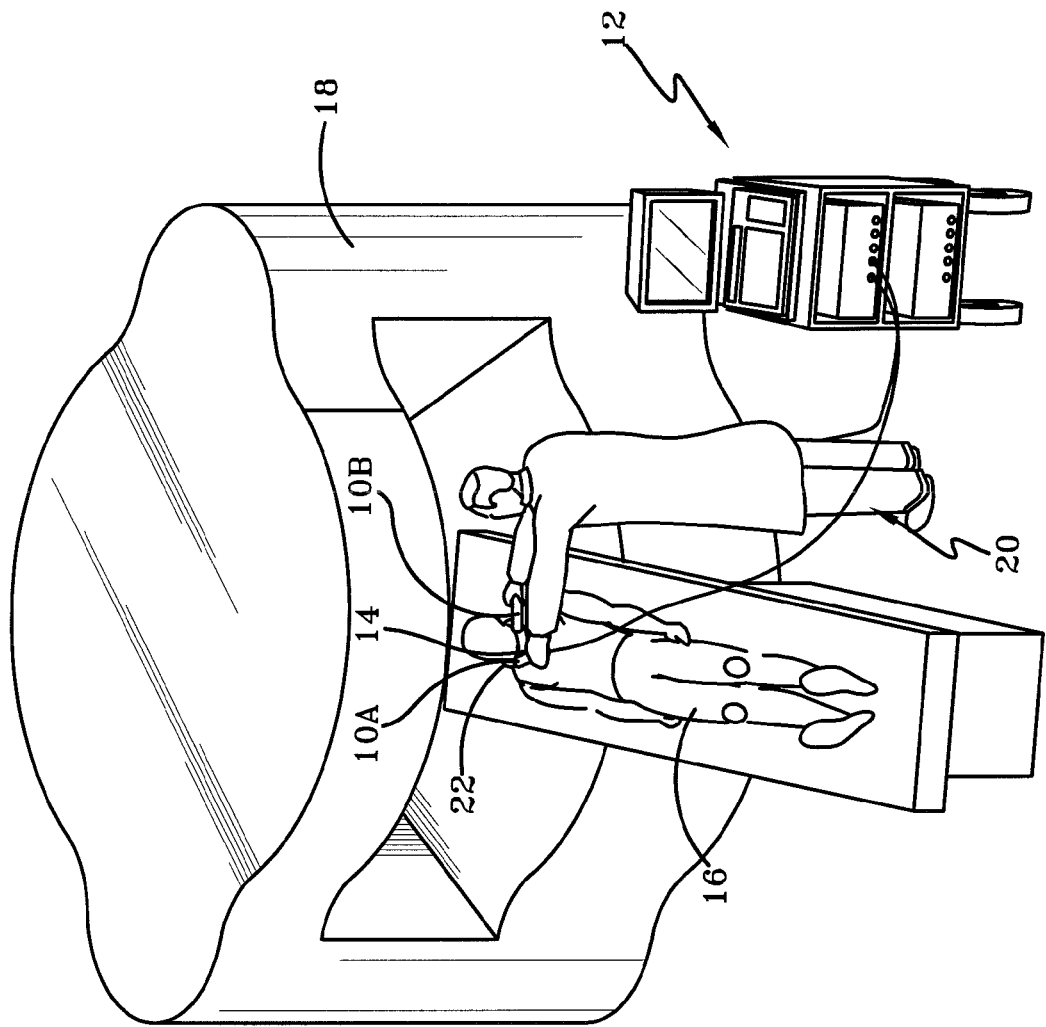
FIG. 2 is a perspective view of a further embodiment of this invention utilizing more than one ultrasound probe for the application of the ultrasound waves.

In a further embodiment of the invention of this application, shown in FIG. 2, more than one source of ultrasound waves may also be used to increase the coverage, depth and power delivered of the waves. Two probes 10A and 10B, or more, may be positioned at preferably different locations, or more preferably opposite locations in the vicinity of portion 14 of body 16 being imaged by MRI Scanner 18. For example, two probes may be used during breast imaging where one probe may be held on either side of the breast, increasing coverage throughout the whole breast, rather than the limited coverage of only one probe on one side of the breast.

Figure 3:
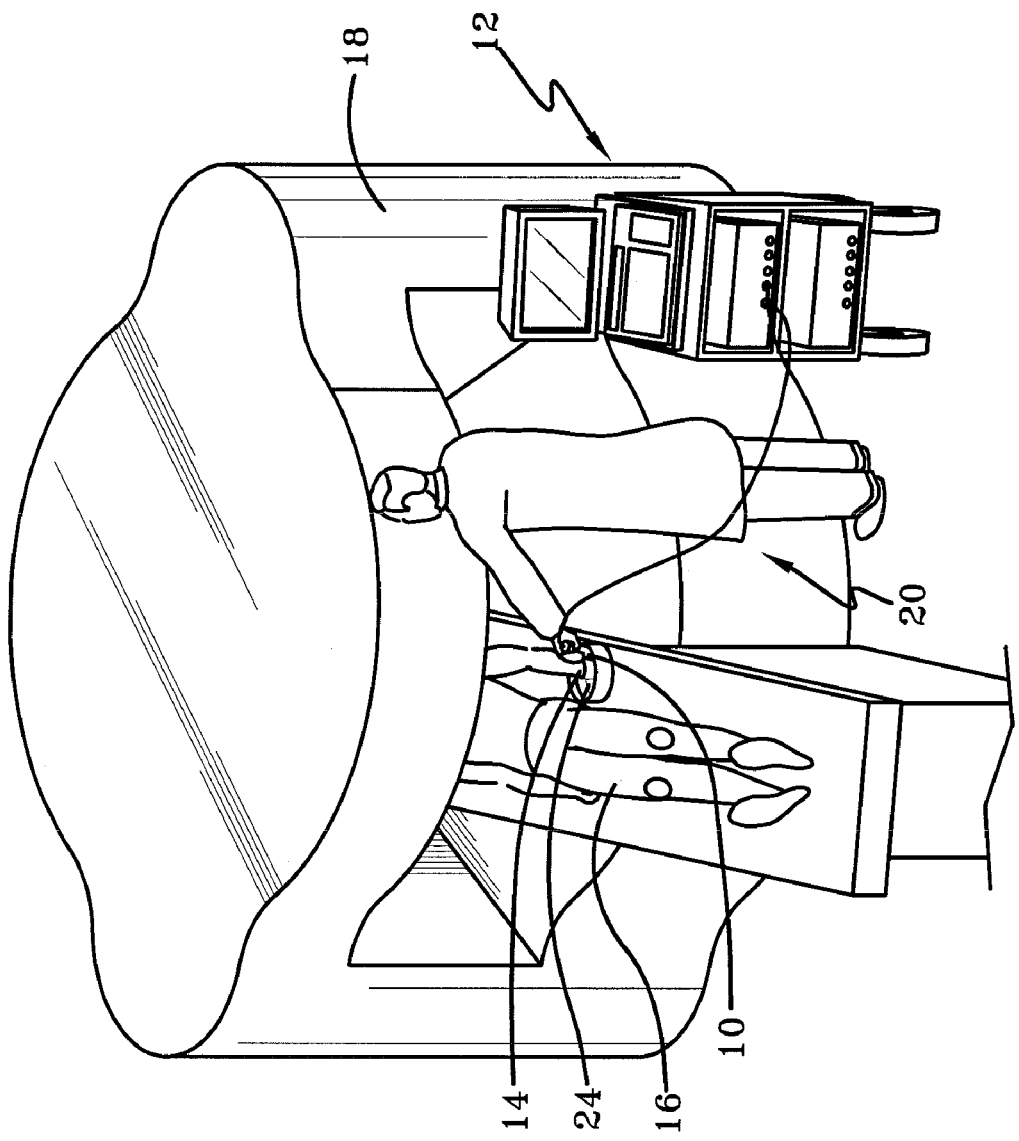
FIG. 3 is a perspective view of yet another embodiment of this invention wherein the portion of the body being imaged is immersed in a water bath.

Yet another embodiment of the invention, shown in FIG. 3, foresees another method of increasing coverage of the ultrasound waves. Portion 14 of body 16 being imaged by MRI Scanner 18 is immersed in water bath 24, and ultrasound probe 10 or probes 10 and 10a apply the high energy ultrasound waves to water bath 24. The complete immersion portion 14 of body 16 causes a uniform distribution of ultrasound waves within water bath 24.

Power levels must be taken into account with all of the above described embodiments of the invention. High duty cycle sequences, multi-slice acquisitions and the gating options that are selected for each image may leave little time during the MR imaging process for application of the ultrasound waves. High levels of ultrasound power may be necessary to induce sufficient relaxation during the short periods of time where it is optimal to apply ultrasound waves, raising concerns of tissue heating in addition to the MR induced tissue heating. In general, the power level should be kept to the minimum level that is effective. However, the concerns of using the occasionally necessary high levels of power are mitigated by the limitation of using ultrasound waves on low to mid-field MRI systems. Low to mid-field MRI systems have inherently low specific absorption rates of MRI induced energy, drastically reducing the risk of tissue heating when even high levels of power are required.

Since the power of ultrasound waves decreases as the depth of penetration increases, the contrast change induced by the ultrasound energy would be non-uniform. There are many methods that can be utilized to improve the uniformity of the contrast. The quantitative properties of ultrasound can be utilized to establish tissue mechanical characteristics from the difference between two differently placed images. Using the quantitative properties of the ultrasound waves may also remove the spatial depth nonuniformity due to ultrasound power loss with distance. Calibration scans may also be utilized to address the non-uniformity of the ultrasound penetration. Multiple located probes and/or multiple power levels may be used, singly or in various combinations in a calibration process to determine induced relaxation changes.

The probe design used for application of the ultrasound waves will also affect the depth of penetration of the ultrasound waves. The design of the probe(s) for the application of ultrasound waves to modify the MR signals should be such that maximum depth and breadth of wave application is possible, as ultrasound waves should also be applied over the broadest area to positively affect the uniformity of coverage of the waves. Probe designs for broad uniform coverage of the ultrasound waves are well known within the ultrasound arts. The electrodes (not shown) used in the probe design may induce image distortions due to the magnetic susceptibility of MR imaging. Using appropriate materials, well known within the art of MR imaging, in the construction of probes 10 and 10a will minimize the image distortions due to susceptibility and other material related issues, such as eddy currents in metal components. The probe location may also be moved away from the imaging region through the use of ultrasound conducting materials between the imaging volume and ultrasound probe(s).

Figure 4:
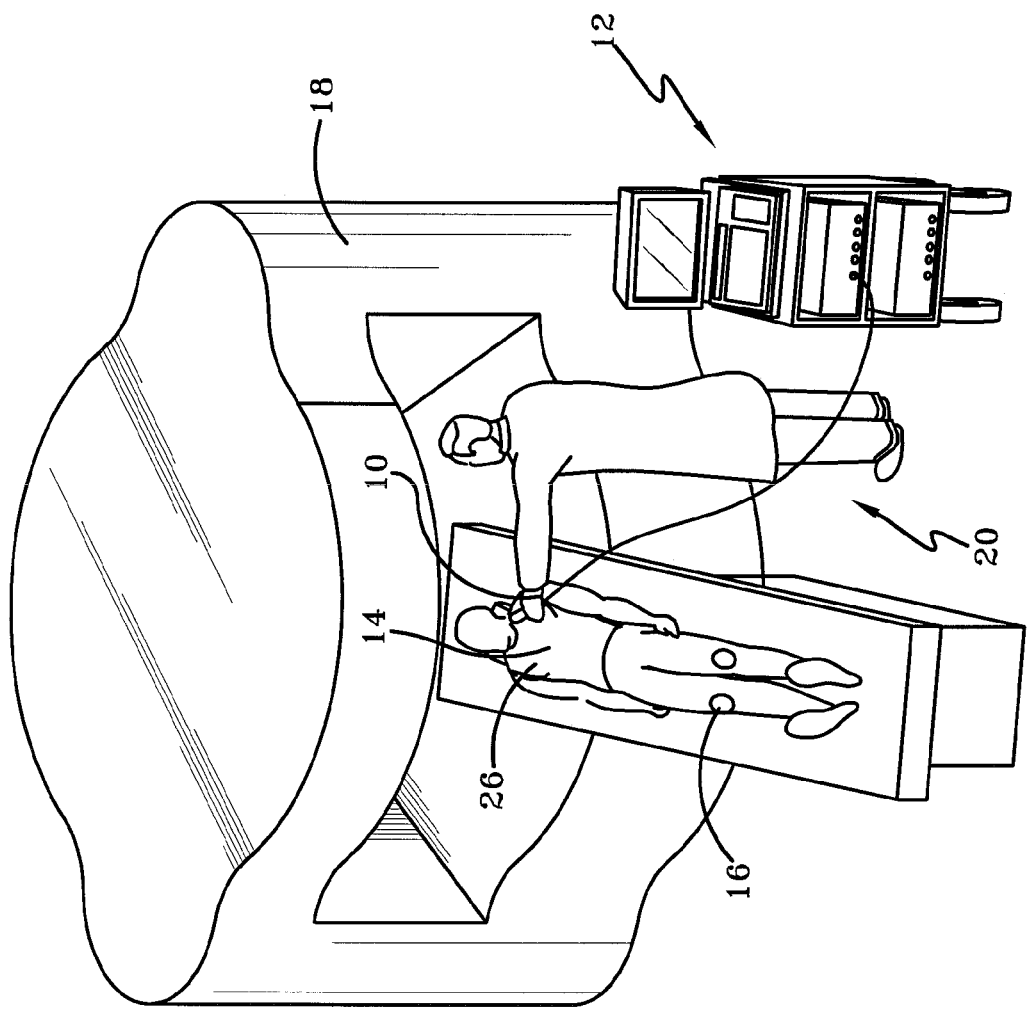
FIG. 4 is a perspective view of an additional embodiment of this invention where a gel bag is placed between the ultrasound probe and the portion of the body of interest.
Figure 5:
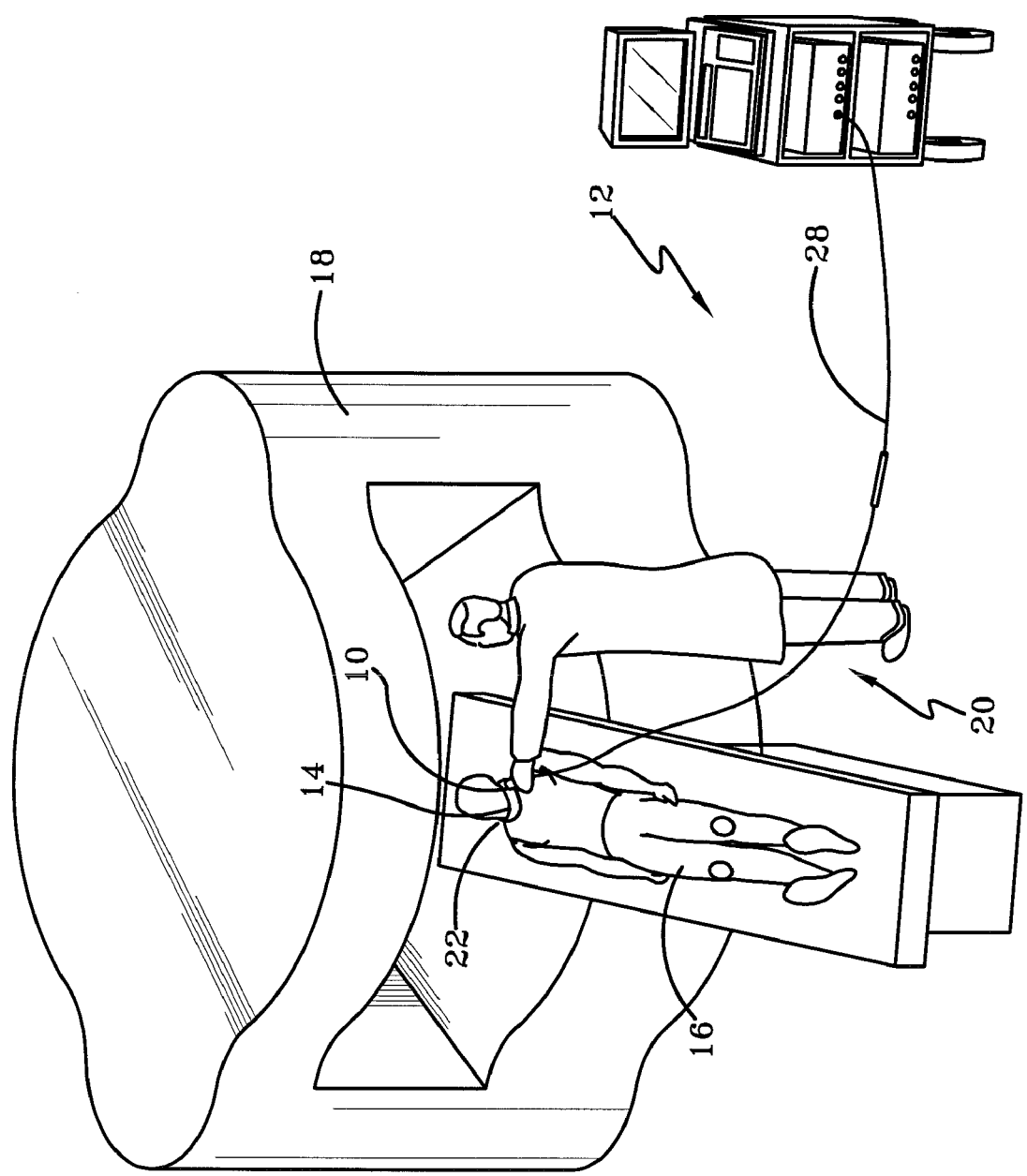
FIG. 5 is a perspective view of an additional embodiment of this invention where an extended connection is used between the ultrasound probe and the ultrasound system.

Probes 10 and 10a may also cause eddy currents that disrupt the uniformity of the MR imaging. If the eddy currents cannot be minimized to be compatible with the ultrasound probe requirements, gel or a gel bag 26, as shown in FIG. 4, may be used in front of the crystal (not shown) within probe 10 to increase the distance from probe 10 to the tissue within portion 14 of body 16, such as the space between probe 10 and the tissue will adequately reduce the magnitude of the artifact. Standard impedance matching probes may also be used, and are well known within the ultrasound arts. The probe design may also necessitate specially designed extended connections 28 to the ultrasound imaging device, for increasing the distance between probe 10 and ultrasound system 12, shown in FIG. 5. This increased distance would effectively reduce any distortion and magnetic artifacts caused by the materials used in the construction of ultrasound system 12.

The nonuniformity of the energy absorption is also affected by the mechanical properties of the tissue being imaged and the consequences of how the ultrasound waves are reflected by the various boundaries between different tissue types, as well as the varying amounts of ultrasound energy absorbed by differing types of tissues. The greater the nonuniformity of energy absorption is affected by tissue characteristics, the more the mechanical characteristics will changes in the MR contrast. Mechanical pressure may be applied to the ultrasound probe to alter the depth and application of the ultrasound waves to a portion of the body being imaged during a portion of the MR imaging sequence, or during the entire imaging sequence.

The frequency at which the ultrasound waves are applied may vary with each application. Image contrast variations will occur if the frequency of the ultrasound waves are substantially the same as the Larmor frequency, or the frequency of the MR signals. In another embodiment of the invention, the frequency of the ultrasound waves applied may differ from the Larmor frequency, or the frequency of the MR signals. Applying ultrasound waves at one frequency away from Larmor, the vibrational characteristics of some components of the tissue molecule may alter the vibrational spectra of other components in near relation to the affected component of the tissue molecule. Further advancements in the technology of ultrasound probes may be necessary before the application of a differing frequency of wave may be possible, as it requires the ultrasound probe to emit an extremely tight spectral range not yet possible by current ultrasound probe designs.

A further aspect of this invention foresees the directional characteristics of ultrasound waves to be utilized as a presaturation (presat) of the MR imaging, causing bands of tissue to be MR suppressed without the use of typical MR preset features. Use of ultrasound waves as a presat feature would improve the sequence duty cycle, and may also improve flow or perfusion imaging.

It is foreseen by this invention that images may be produced by ultrasound imaging simultaneously with the MR imaging during various embodiments of this invention. Simultaneously capturing an ultrasound and MR image has many benefits, including the identical registration and positioning of the patient and decreased time of scanning as only one imaging set would be necessary instead of two. Capturing MR and ultrasound images simultaneous is possible in situations where the frequency of both image types is identical, or substantially similar such that the ultrasound frequency does not impair the MR imaging, or cause artifacts in the MR images. The ultrasound waves and MR signals create a symbiotic relationship allowing unique images to be collected simultaneously.

It is foreseen by this invention that specific contrast agents may be used during various embodiments of this invention. Current commonly used contrast agents such as Gd-DTPA may be used in the simultaneous imaging. New contrast agent formulations may also be created to utilize the unique characteristics of ultrasound waves combined with MR signals. Ultrasound bubble contrast agents may be used with narrow beam ultrasound applications, as different susceptibility patterns may be noticed when the ultrasound waves pop the bubbles open at the desired location. Variations may be available for use with broad beam applications as well.

Described above is a medical imaging technique that includes directing ultrasound waves into a portion of a body of interest during at least a portion of a time period during which an MR imaging process is simultaneously performed on the portion of the body of interest. The waves may be applied continually during the MR imaging process, or only during a portion thereof. The frequency of the ultrasound waves may be substantially the same as, or different than that of the MR signals.

In the foregoing description, certain terms have been used for brevity, clearness, illustration and understanding; but no unnecessary limitations are to be implied therefrom beyond the requirements of the prior art, because such terms are used for descriptive purposes and are intended to be broadly construed. Moreover, this invention has been described in detail with reference to specific embodiments thereof, including the respective best modes for carrying out each embodiment. It shall be understood that these illustrations are by way of example and not by way of limitation.

What is claimed is:

1. A medical imaging technique comprising:
   performing at least one of a low-field and mid-field magnetic resonance (MR) imaging process on a portion of a body of interest over a time period; and
   simultaneously directing ultrasound waves at a Larmor frequency of the MR imaging process into the portion of the body of interest during at least a portion of the time period to modify a spin-lattice relaxation time of the portion of the body of interest, thereby altering contrast discrimination in images generated from the MR imaging process.

2. The medical imaging technique of claim 1 wherein said ultrasound waves are directed continuously throughout the entire duration of said time period.

3. The medical imaging technique of claim 1 wherein the ultrasound waves are directed at a first power level during at least a portion of a time period when no RF signal is being applied during the MR imaging process and the ultrasound waves are directed at a second power level during at least a portion of a time period when RF signals are applied during the MR imaging process.

4. The medical imaging method of claim 1 wherein the ultrasound waves are directed at a first power level during at least a portion of a time period when no data sampling occurs during the MR imaging process and the ultrasound waves are directed at a second power level during at least a portion of a time period when data sampling occurs during the MR imaging process.

5. The medical imaging technique of claim 1 further comprising producing clinical images from both the application of said ultrasound waves as well as said MR imaging process.

6. The medical imaging technique of claim 1 wherein more than one source of ultrasound waves is utilized to direct said ultrasound waves into said portion of the body of interest.

7. The medical imaging technique of claim 1 which further comprises the injection of a contrast agent into said body of interest prior to said MR imaging process.

8. The medical imaging technique of claim 1 wherein an ultrasound distribution medium is used within close proximity of said portion of the body of interest.

* * * * *